United States Patent
DeSimone et al.

(10) Patent No.: US 6,271,241 B1
(45) Date of Patent: Aug. 7, 2001

(54) CYCLOALKYL AND ARYL FUSED AMINOALKYL-IMIDAZOLE DERIVATIVES: MODULATORS AND GLP-1 RECEPTORS

(75) Inventors: Robert W. DeSimone, Durham; Alan Hutchison, Madison, both of CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 09/539,835

(22) Filed: Mar. 31, 2000

Related U.S. Application Data

(60) Provisional application No. 60/127,656, filed on Apr. 2, 1999.

(51) Int. Cl.$^7$ ............... A61K 31/435; A61K 31/415; C07D 235/16; C07D 471/04
(52) U.S. Cl. ............... 514/303; 514/338; 514/394; 436/63; 544/236; 544/335; 544/350; 548/252; 548/266.4; 548/309.7; 546/118; 546/273.4
(58) Field of Search ............... 548/309.7, 252, 548/266.4; 546/118, 273.4; 544/236, 335, 350; 514/303, 338, 394; 436/63

(56) References Cited

U.S. PATENT DOCUMENTS

| | | | |
|---|---|---|---|
| 3,255,202 | 6/1966 | Johnson | 260/309.2 |
| 3,455,940 | 7/1969 | Stecker | 260/295 |
| 3,905,990 | 9/1975 | Ehrmann et al. | 260/309.2 |
| 3,941,788 | 3/1976 | Hankovsky et al. | 260/256.4 F |
| 3,995,044 | 11/1976 | Kabbe et al. | 424/263 |
| 5,066,576 | 11/1991 | Ichijima et al. | 430/558 |
| 5,296,339 | 3/1994 | Fujita et al. | 430/389 |
| 5,789,428 | 8/1998 | Shibata et al. | 514/367 |
| 5,877,195 | 3/1999 | Lukenheimer et al. | 514/394 |

FOREIGN PATENT DOCUMENTS

| | | |
|---|---|---|
| 0 598 962 | 6/1994 | (EP). |
| 0 616 807 | 9/1994 | (EP). |
| 0 882 718 | 12/1998 | (EP). |
| 1 501 151 | 10/1966 | (FR). |
| 7-133224 | 5/1995 | (JP). |
| WO 96/00730 | 1/1996 | (WO). |
| WO 96/33191 | 10/1996 | (WO). |
| WO 96/33194 | 10/1996 | (WO). |
| WO 96/39404 | 12/1996 | (WO). |
| WO 97/24119 | 7/1997 | (WO). |
| WO 98/17651 | 4/1998 | (WO). |
| WO 98/45295 | 10/1998 | (WO). |
| WO 99/37303 | 7/1999 | (WO). |
| WO 99/47131 | 9/1999 | (WO). |
| WO 99/47142 | 9/1999 | (WO). |
| WO 99/47171 | 9/1999 | (WO). |

OTHER PUBLICATIONS

V.M. Aryuzina et al., "The Synthesis of Substitution Products of 4H–Imidazo[5,1–b]Benzimidazole, V*. Some Substitution Reactions of 1,4,–Dimethyl and 1–Phenyl–4–Methylimidazo–[5,1–b]Benzimidazoles", *Chemistry of Heterocyclic Compounds*, 1970, vol. 4, pp. 526–528.

V.M. Aryuzina et al., "Synthesis of 4H–Imidazo[5,1–a] Benzimidazole Substituents, VIII*, Synthesis of 1–Phenyl–4–Benzylimidazol[5,1–a]Benzimidazole and Some of Its 3–Substituents", *Chemistry of Heterocyclic Compounds*, No. 3, 1973, pp. 395–397.

*Chemical Abstracts*, vol. 73, No. 17, abstract No. 87845h. (Oct 26, 1970).

*Chemical Abstracts*, vol. 127, No. 3, abstract No. 34242m, col. 650. (Jul. 21, 1997).

Cristos T.E. et al., "Corticotrophin–releasing factor receptor antagonists", *Expert Opinion on Therapeutic Patents*, vol. 8, No. 2, Feb. 1998 (1998–02), pp. 143–152, XP002109498.

*Primary Examiner*—Bernard Dentz
(74) *Attorney, Agent, or Firm*—McDonnell Boehnen Hulbert & Berghoff; Steven J. Sarussi

(57) ABSTRACT

Disclosed are compounds of the formula:

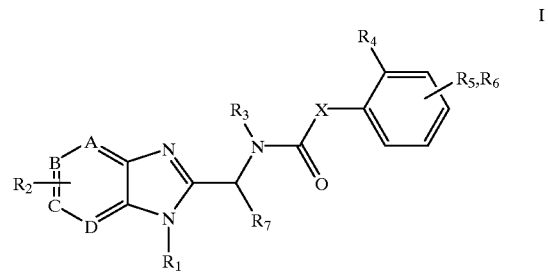

or the pharmaceutically acceptable non-toxic salts thereof wherein X, $R_1$, $R_2$, $R_3$, $R_4$, $R_5$, $R_6$, $R_7$, A, B, C, and D are variables defined herein. Such compounds useful in treatment of obesity and diabetes. The invention also provides labeled probes for the localization of cellular receptors that are involved in the modulation of blood glucose levels.

51 Claims, No Drawings

CYCLOALKYL AND ARYL FUSED AMINOALKYL-IMIDAZOLE DERIVATIVES: MODULATORS AND GLP-1 RECEPTORS

This application claims the benefit of U.S. Provisional Application No. 60/127,656, filed on Apr. 2, 1999.

BACKGROUND OF THE INVENTION

1. Field of the Invention

This invention relates to 1-benzylimidazole derivatives, and more specifically, to the use of such compounds as pharmaceutical agents, e.g., as modulators of blood glucose levels. This invention also relates to pharmaceutical compositions comprising such compounds and to the use of such compounds in treating a variety of disorders associated with feeding and food metabolism. Additionally, this invention relates to the use such compounds as probes for the localization of cellular receptors that are involved in the modulation of blood glucose levels.

2. Background

Diabetes mellitus is a chronic syndrome of impaired carbohydrate and fat metabolism resulting from insufficient insulin secretion and/or target tissue insulin resistance. It occurs in two major forms: insulin-dependent diabetes mellitus (IDDM, Type 1) and non-insulin-dependent diabetes mellitus (NIDDM, Type 2). These forms differ in their etiology, age of onset and treatment. Type 1 is often characterized by onset during childhood and the patients typically become fully dependent upon exogenous insulin to sustain life. The disorder is associated with a lack of insulin production by the pancreatic Islets of Langerhans. The disease is generally marked by a drastic reduction in the number of insulin secreting islet beta cells.

NIDDM usually appears later in life (age 40–60) and is often associated with obesity. Patients with NIDDM show normal basal levels of insulin but display an abnormal insulin secretion response (delayed or reduced) to a glucose load. As the disease progresses, insulin target tissues show signs of diminished response to insulin (insulin resistance). Effective treatment of the disorder is usually obtained by dietary control, with or without the use of oral hypoglycemic drugs. Sulphonylureas are a class of hypoglycemic compounds used in the treatment of NIDDM. These drugs exert their action by causing insulin to be released from intracellular stores. Care must be taken in the administration of these agents in order to not induce severe hypoglycemia due to excessive insulin release. In addition, overdose may deplete insulin stores to a point requiring administration of exogenous insulin.

The discovery that glucose administered via the gastrointestinal tract provides greater stimulation of insulin release than a comparable glucose challenge given intravenously led to the identification of certain gut secreted 'incretin' hormones which augment glucose stimulated insulin secretion, and the identification of specific cell surface receptors that modulate the effects of such incretin hormones. Glucagon-like Peptide-1 (7–36)-amide (GLP-1) is one such incretin hormone that is secreted from gastrointestinal L cells in response to food intake and increases insulin secretion from pancreatic beta cells (Fehmann, H. C.; Goke, R. and Goke, B. (1995) *Endocr. Rev.* 16: 390–410). GLP-1 exerts its actions via binding to a G-protein-linked receptor expressed in islet β-cells.

Unlike the sulphonylureas, the effects of GLP-1 are dependent upon plasma glucose concentration in that the insulinotropic effects of GLP-1 are abolished at low plasma glucose levels. In addition to its stimulation of insulin secretion, GLP-1 also increases insulin synthesis (Drucker, D. J. (1987) *Proc. Natl Acad. Sci USA* 84: 3434–3438), inhibits glucagon secretion (Kawai (1989) *Endocrinology* 124: 1768–1773) and delays gastric emptying (Nauck, Md. (1995) *Gut* 37(2): A124). This combination of actions gives GLP-1 unique potential therapeutic advantages over other agents presently used to treat non-insulin dependent diabetes mellitus. In a clinical trial of patients with NIDDM it was found that subcutaneous administration of GLP-1 could normalize postprandial glucose levels (Todd et al. (1997) *Eur. J. Clin. Invest.* 27: 533–536). Drugs that mimic the action of GLP-1, i.e. stimulate insulin secretion from pancreatic β-cells, but only at higher than normal blood gluose levels, are particularly desirable for us in the treatment of NIDDM. Such drugs may work by modulating the signal-transducing activity of the GLP-1 receptor.

In clinical studies GLP-1 has been shown to reduce appetite and increase satiety in both normal weight and obese subjects (see, e.g., Christophe *J. Ann. N Y Acad. Sci.* (1998) 865:323–335 and Gutwiller, J. P., *Am. J. Physio.* (1999) 276: R1541–1544). Thus drugs that modulate the activity of the GLP-1 receptor may be useful for the treatment of obesity and eating disorders.

The effect of a compound on blood glucose levels can be determined in vivo, through the use a glucose tolerance test, in which the blood glucose levels laboratory animals subjected to a glucose challenge are monitored in the presence and absence of the compound. The effects of test compounds on glucose tolerance may be evaluated in non-diabetic laboratory animals as discussed in Wang et al., *J. Clin. Invest.* (1995) 95: 417–421 and Holst, *Curr. Opinion in Endocrinology* and *Diabetes* (1998) 5: 108–115.

Alternatively, the effects of test compounds on blood glucose levels may be assessed in an animal model of diabetes, e.g., streptozotocin (STZ)-induced diabetes. Such assays have been disclosed by Tancrède et al. (*Br. J. Exp. Path.* (1983) 64: 117–123), Junod et al. (*J. Clin. Inv.* (1969) 48: 2129–2139, Rondu et al. (*J. Med. Chem.* (1997) 40:3793–3803), and Maloff and Boyd (*Diabetologia* (1986) 29: 295–300).

In vitro experiments that monitor the interaction of the compound with GLP-1 receptors may also be used to reliably predict the effects of a compound on blood glucose levels. In one such experiment the interaction of compounds with GLP-1 receptors, expressed either recombinantly or naturally in high abundance in certain cell lines, may be determined by a cell-based luciferase screen or by binding experiments measuring competition binding e.g., with a labeled GLP-1 ligand such as GLP-1 or GLP(7–36) peptide.

Receptors that are coupled to the $G_s$ stimulatory G-protein subunit transduce intracellular signals via the adenylate cyclase pathway. Stimulation of these receptors with an agonist typically results in an elevation of cytoplasmic cAMP levels which can trigger the subsequent transcription of a variety of genes, generally those with promoters containing binding sites (cAMP responsive elements—CREs) for the transcription factor, CREB (CRE binding protein).

Receptor modulation may be measured via measurement of transcriptional activation of a firefly luciferase reporter gene. Such an assay may use a Chinese hamster ovary cell line (CHO-K1) stably transfected with a GLP-1 receptor (a $G_s$ coupled receptor) expression plasmid and a luciferase reporter plasmid, wherein luciferase expression is under the transcriptional control of multiple CREs. In these cell lines, the GLP1 agonist GLP(7–36) peptide stimulates luciferase expression in a dose dependent manner with a potency ($EC_{50}$~20 pM) similar to the data reported by Gromada et al. (1995) *FEBS Lett.* 373: 182–186.

Compounds are screened by seeding 15,000 cells per well in opaque multi-well plates. Cells are then incubated overnight in a tissue culture incubator. Compounds are dispensed to a final concentration of 4 uM in 1% DMSO. After 6 hours of incubation, cells are assayed for luciferase activity, which is measured in a luminometer.

SUMMARY OF THE INVENTION

This invention provides compounds of Formula I, below. The invention also provides compounds of Formula I that bind specifically, and preferably with high affinity, to specific cellular receptors. Preferably the receptors are cell surface receptors, and more preferably G-protein coupled receptors. Even more preferably, the receptors are Secretin-like receptors. Highly preferred receptors are GLP receptors, and most preferably, the receptors are GLP-1 receptors. Such compounds are useful in the treatment of diabetes, especially non-insulin-dependent diabetes mellitus (Type 2 diabetes), and in the treatment of obesity and eating disorders.

The invention further comprises methods of treating patients suffering from diabetes, especially non-insulin-dependent diabetes mellitus (Type 2 diabetes), obesity or eating disorders by administering to a patient in need of such treatment an effective amount of a compound of the invention. Treatment of human patients, domesticated companion animals (pets) or livestock animals suffering from these disorders with an effective amount of a compound of the invention is encompassed by the invention.

In a separate aspect, this invention provides compounds that are useful as probes for the localization of specific receptors. Preferably these receptors modulate blood glucose levels. Such receptors are preferably so localized in tissue samples, especially tissue sections. Such probes are also useful for measuring levels of such receptors expressed in tissue samples or cell membrane preparations of tissue samples and for localizing receptors in living patients (e.g., via PET scanning).

The invention also comprises a method for altering the signal-transducing activity of a cell surface GLP1 receptor, said method comprising exposing cells expressing such a receptor to an effective amount of a compound of the Formula I, below.

The invention also provides pharmaceutical compositions comprising compounds of Formula I, including packaged pharmaceutical compositions. Packages pharmaceutical compositions may include a container and instructions for using the composition to treat a patient in need thereof. Particulary, the invention includes packaged pharmaceutical compositions that include a container and instructions for using the composition to treat a patient suffering from diabetes, obesity or eating disorders.

Accordingly, a broad embodiment of the invention is directed to compounds of Formula I:

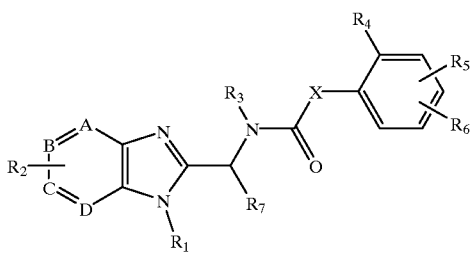

or the pharmaceutically acceptable non-toxic salts thereof wherein:
$R_7$ represents H, or $C_1$–$C_6$ alkyl;
when $R_7$ is H, $R_1$ represents 2-, 3-, or 4-picolyl or benzyl, each of which is optionally mono-, di-, or trisubstituted independently with
halogen, nitro, trifluoromethyl, cyano, hydroxyl, $C_1$–C6 alkoxy, or $C_1$–$C_6$ alkyl;
amino, mono or di($C_1$–$C_6$)alkylamino, amino($C_1$–C6) alkyl, or mono- or di($C_1$–$C_6$)alkylamino($C_1$–$C_6$) alkyl, or mono- or di($C_1$–$C_6$)alkylamino($C_1$–$C_6$) alkoxy;
—O($CH_2$)$_n$$CO_2$$R_8$ where n is 1, 2, 3 or 4, $NR_8COR_9$, $COR_8$, $CONR_8R_9$ or $CO_2R_8$ where $R_8$ and $R_9$ are the same or different and represent hydrogen or $C_1$–$C_6$ alkyl; or
$NR_8R_9$ forms a 5-, 6- or 7-membered heterocycloalkyl ring;
$SO_2R_8$, $NHSO_2R_8$, $SO_2NHR_8$, $SO_2NHCOR_8$, $CONHSO_2R_8$ where $R_8$ is as defined above;
O($CH_2$)$_n$—G where n=1, 2, 3 or 4 and G represents $SO_2R_8$, $NHSO_2R_8$, $SO_2NHR_8$, $SO_2NHCOR_8$, $CONHSO_2R_8$, where $R_8$ is as defined above; or
tetrazole, triazole, imidazole, thiazole, oxazole, thiophene, or pyridyl;
when $R_7$ represents $C_1$–$C_6$ alkyl, $R_1$ represents $C_1$–$C_6$ alkyl, cyclopentyl, or cyclopropylmethyl; or $R_1$ represents benzyl optionally mono-, di, or trisubstituted independently with halogen, nitro, trifluoromethyl, cyano, hydroxyl, $C_1$–$C_6$ alkoxy, or $C_1$–$C_6$ alkyl; or amino, mono or di($C_1$–$C_6$)alkylamino, amino($C_1$–$C_6$) alkyl, or mono- or di($C_1$–$C_6$)alkylamino($C_1$–$C_6$)alkyl, or mono- or di($C_1$–$C_6$)alkylamino($C_1$–$C_6$)alkoxy;
$R_2$ represents
hydrogen or hydroxy;
$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
O($CH_2$)$_n$$CO_2$$R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl; or
$NR_8R_9$ forms 5-, 6-, or 7-membered heterocyclic ring;
$R_3$ represents $C_1$–$C_6$ alkyl;
$R_4$ represents $C_1$–$C_6$ alkoxy; or
$R_4$ represents methyl when $R_1$ and $R_7$ are lower alkyl;
$R_5$ and $R_6$ are the same or different and represent hydrogen or halogen;
$C_1$–$C_6$ alkyl or $C_1$–$C_6$ alkoxy, the alkyl portion of each being optionally substituted with amino, mono- or di($C_{1–6}$) alkylamino, or a $C_5$–$C_7$ heterocycloalkyl group where the heteroatom is nitrogen and the nitrogen is attached to the parent alkyl portion;

O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or straight or branched chain lower alkyl having 1–6 carbon atoms;

NR$_8$R$_9$ forms a 5-, 6- or 7-membered heterocyclic ring;

X represents a bond, CH$_2$O, or CH=CH; and

A, B, C, and D independently represent CH or N with the proviso that not more than two of A, B, C and D represent N.

These compounds are useful in the diagnosis and treatment of obesity and diabetes.

DETAILED DESCRIPTION OF THE INVENTION

The compounds of the instant invention are represented by the formula I:

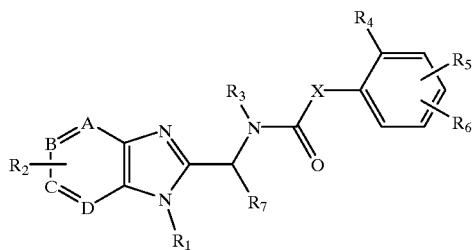

I or pharmaceutically acceptable non-toxic salts thereof wherein:

R$_7$ represents H, or C$_1$–C$_6$ alkyl;

when R$_7$ is H, R$_1$ represents 2-, 3-, or 4-picolyl or benzyl, each of which is optionally mono-, di-, or trisubstituted independently with halogen, nitro, trifluoromethyl, cyano, hydroxyl, C$_1$–C$_6$ alkoxy, or C$_1$–C$_6$ alkyl;

amino, mono or di(C$_1$–C$_6$)alkylamino, amino(C$_1$–C$_6$) alkyl, or mono- or di(C$_1$–C$_6$)alkylamino(C$_1$–C$_6$) alkyl, or mono- or di(C$_1$–C$_6$)alkylamino (C$_1$–C$_6$) alkoxy;

—O(CH$_2$)$_n$CO$_2$R$_8$ where n is 1, 2, 3 or 4 NR$_8$COR$_9$, COR$_8$, CONR$_8$R$_9$ or CO$_2$R$_8$ where R$_8$ and R$_9$ are the same or different and represent hydrogen or C$_1$–C$_6$ alkyl; or NR$_8$R$_9$ forms a 5-, 6- or 7-membered heterocycloalkyl ring;

SO$_2$R$_8$, NHSO$_2$R$_8$, SO$_2$NHR$_8$, SO$_2$NHCOR$_8$, CONHSO$_2$R$_8$ where R$_8$ is as defined above;

O(CH$_2$)$_n$—G where n=1, 2, 3 or 4 and G represents SO$_2$R$_8$, NHSO$_2$R$_8$, SO$_2$NHR$_8$, SO$_2$NHCOR$_8$, CONHSO$_2$R$_8$, where R$_8$ is as defined above; or tetrazole, triazole, imidazole, thiazole, oxazole, thiophene, or pyridyl;

when R$_7$ represents C$_1$–C$_6$ alkyl, R$_1$, represents C$_1$–C$_6$ alkyl, cyclopentyl, or cyclopropylmethyl; or R$_1$ represents benzyl optionally mono-, di, or trisubstituted independently with halogen, nitro, trifluoromethyl, cyano, hydroxyl, C$_1$–C$_6$ alkoxy, or C$_1$–C$_6$ alkyl; or amino, mono or di(C$_1$–C$_6$)alkylamino, amino(C$_1$–C$_6$) alkyl, or mono- or di(C$_1$–C$_6$)alkylamino(C$_1$–C$_6$)alkyl, or mono- or di(C$_1$–C$_6$)alkylamino(C$_1$–C$_6$)alkoxy;

R$_2$ represents hydrogen or hydroxy;

C$_1$–C$_6$, alkyl or C$_1$–C$_6$ alkoxy, each of which is optionally substituted with amino or mono- or di(C$_1$–C$_6$) alkylamino, C$_5$–C$_7$ cycloalkylamino or C$_5$–C$_7$ cycloalkoxy; or O(CH$_2$)$_n$CO$_2$R$_8$ where n=1, 2, 3 or 4 NR$_8$COR$_9$, COR$_8$, CONR$_8$R$_9$ or CO$_2$R$_8$ where R$_8$ and R$_9$ are the same or different and represent hydrogen or C$_1$–C$_6$ alkyl; or NR$_8$R$_9$ forms 5-, 6-, or 7-membered heterocyclic ring;

R$_3$ represents C$_1$–C$_6$ alkyl;

R$_4$ represents C$_1$–C$_6$ alkoxy; or

R$_4$ represents methyl when R$_1$ and R$_7$ are lower alkyl;

R$_5$ and R$_6$ are the same or different and represent hydrogen or halogen;

C$_1$–C$_6$ alkyl or C$_1$–C$_6$ alkoxy, the alkyl portion of each being optionally substituted with amino, mono- or di(C$_1$–C$_6$) alkylamino, or a C$_5$–C$_7$ heterocycloalkyl group where the heteroatom is nitrogen and the nitrogen is attached to the parent alkyl portion;

O(CH$_2$)$_n$CO$_2$R$_8$ where n=1, 2, 3 or 4 NR$_8$COR$_9$, COR$_8$, CONR$_8$R$_9$ or CO$_2$R$_8$ where R$_8$ and R$_9$ are the same or different and represent hydrogen or straight or branched chain lower alkyl having 1–6 carbon atoms;

NR$_8$R$_9$ forms a 5-, 6- or 7-membered heterocyclic ring;

X represents a bond, CH$_2$O, or CHCH; and

A, B, C, and D are the same or different and represent CH or N with the proviso that not more than two of A, B, C and D represent N.

Preferred compounds of the invention are represented by Formula II

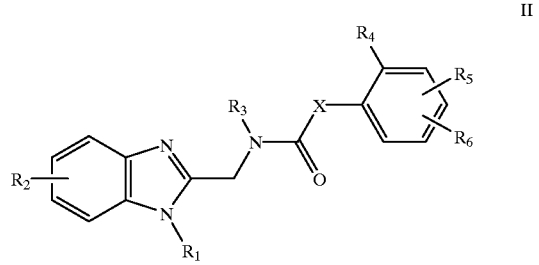

II where

R$_1$ represents benzyl optionally mono-, di-, or trisubstituted independently with halogen, nitro, trifluoromethyl, cyano, hydroxyl, C$_1$–C$_6$ alkoxy, or C$_1$–C$_6$alkyl; or amino, mono or di(C$_1$–C$_6$ )alkylamino, amino(C$_1$–C$_6$ )alkyl, or mono- or di(C$_1$–C$_6$)alkylamino(C$_1$–C$_6$) alkyl, or mono- or di(C$_1$–C$_6$)alkylamino(C$_1$–C$_6$) alkoxy; with the proviso that R$_1$ is not 3-fluorobenzyl;

R$_2$ represents hydrogen or hydroxy;

C$_1$–C$_6$ alkyl or C$_1$–C$_6$ alkoxy, each of which is optionally substituted with amino or mono- or di(C$_1$–C$_6$) alkylamino, C$_5$–C$_7$ cycloalkylamino or C$_5$–C$_7$ cycloalkoxy; or O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or C$_1$–C$_6$ alkyl; or NR$_8$R$_9$ forms 5-, 6-, or 7-membered heterocyclic ring;

R$_3$ represents C$_1$–C$_6$ alkyl;

R$_4$ represents C$_1$–C$_6$ alkoxy;

R$_5$ and R$_6$ are the same or different and represent hydrogen or halogen;

$C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion; and X represents a bond or $CH_2O$.

Preferred compounds of Formula II include those where one of $R_5$ and $R_6$ is hydrogen. Other preferred compounds of II are those where $R_4$ is methoxy, one of $R_5$ and $R_6$ is hydrogen, and the other of $R_5$ and $R_6$ is alkoxy. Still other preferred compounds of II are those where $R_7$ is $C_4$–$C_6$ alkyl.

More preferred compounds of Formula II include those where wherein X is a bond. Other more preferred compounds of II are those where $R_1$ is benzyl monosubstituted in the ortho position.

Other preferred compounds of the invention are represented by Formula III

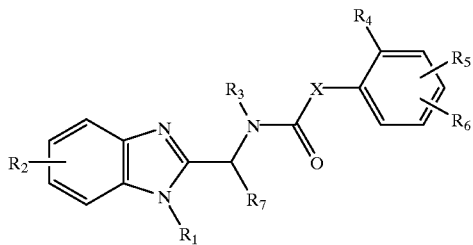

III wherein:

$R_7$ represents $C_1$–$C_6$ alkyl;

$R_1$ represents $C_1$–$C_6$ alkyl, cyclopentyl, or cyclopropylmethyl;

$R_2$ represents hydrogen or hydroxy;

$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or $O(CH_2)_nCO_2R_8$ where n=1, 2, 3 or 4 $NR_8COR_9$, $COR_8$, $CONR_8R_9$ or $CO_{2S}$ where $R_8$ and $R_9$ are the same or different and represent hydrogen or $C_1$–$C_6$ alkyl; or $NR_8R_9$ forms 5-, 6-, or 7-membered heterocyclic ring;

$R_3$ represents $C_1$–$C_6$ alkyl;

$R_4$ represents $C_1$–$C_6$ alkoxy; or $R_4$ represents methyl when $R_1$ and $R_7$ are lower alkyl;

$R_5$ and $R_6$ are the same or different and represent hydrogen or halogen;

$C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion;

$O(CH_2)_nCO_2R_8$ where n=1, 2, 3 or 4 $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms;

$NR_8R_9$ forms a 5-, 6- or 7-membered heterocyclic ring;

X represents a bond or $CH_2O$.

Preferred compounds of Formula III include those where $R_3$ and $R_7$ are methyl. Other preferred compounds of Formula III are those where $R_1$ is propyl or cyclopropylmethyl. Still other preferred compounds of III are those where $R_1$ is cyclopentyl.

Particularly preferred compounds of Formula III include those where X is $CH_2O$. Other particularly preferred compounds of III are those where $R_1$ is propyl or cyclopropylmethyl. Still other particularly preferred compounds of Formula III are those where $R_1$ is propyl or cyclopropylmethyl and one of $R_5$ and $R_6$ is hydrogen. Other particularly preferred compounds of Formula III are those where $R_1$ is propyl, $R_4$ is methoxy or methyl, one of $R_5$ and $R_6$ is hydrogen, and the other of $R_5$ and $R_6$ is alkoxy.

Other preferred compounds of the invention are represented by Formula IV

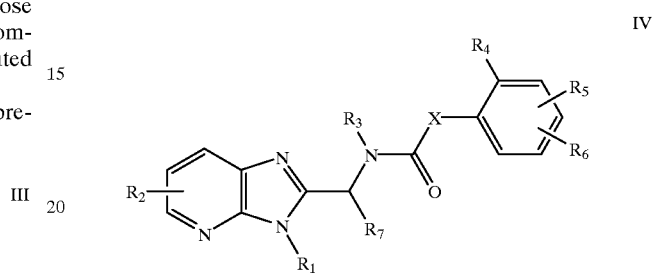

IV wherein:

$R_7$ represents $C_1$–$C_6$ alkyl;

$R_1$ represents $C_1$–$C_6$ alkyl, cyclopentyl, or cyclopropylmethyl;

$R_2$ represents hydrogen or hydroxy;

$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or $O(CH_2)_nCO_2R_8$ where n=1, 2, 3 or 4 $NR_8COR_9$, $COR_8$, $CONR_8R_9$ or $CO_2R_8$ where $R_8$ and $R_9$ are the same or different and represent hydrogen or $C_1$–$C_6$ alkyl; or $NR_8R_9$ forms 5-, 6-, or 7-membered heterocyclic ring;

$R_3$ represents $C_1$–$C_6$ alkyl;

$R_4$ represents $C_1$–$C_6$ alkoxy; or $R_4$ can represent methyl when $R_1$ and $R_7$ are lower alkyl;

$R_5$ and $R_6$ are the same or different and represent hydrogen or halogen;

$C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion;

$O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms;

$NR_8R_9$ forms a 5-, 6- or 7-membered heterocyclic ring;

X represents a bond or $CH_2O$.

Preferred compounds of Formula IV are those where $R_3$ and $R_7$ are methyl. Other preferred compounds of IV are those where $R_1$ is propyl or cyclopropylmethyl. Still other preferred compounds of Formula IV are those where $R_1$ is cyclopentyl. Yet other preferred compounds of IV include those where X is $CH_2O$.

More preferred compounds of IV are those wherein $R_1$ is propyl or cyclopropylmethyl. Particularly preferred compounds of Formula IV are those where $R_1$ is propyl or cyclopropylmethyl and one of $R_5$ and $R_6$ is hydrogen. Still other particularly preferred compounds of IV include those where $R_1$ is propyl, $R_4$ is methoxy or methyl, one of $R_5$ and $R_6$ is hydrogen, and the other of $R_5$ and $R_6$ is alkoxy.

Other preferred compounds of the invention are represented by Formula V

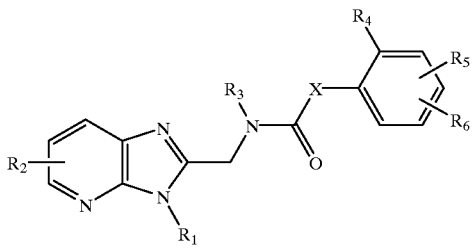

where $R_1$ represents benzyl optionally mono-, di-, or trisubstituted independently with
halogen, nitro, trifluoromethyl, cyano, hydroxyl, $C_1$–$C_6$ alkoxy, or $C_1$–$C_6$ alkyl; or
amino, mono or di($C_1$–$C_6$)alkylamino, amino($C_1$–$C_6$) alkyl, or mono- or di($C_1$–$C_6$)alkylamino($C_1$–$C_6$) alkyl, or mono- or di($C_1$–$C_6$)alkylamino($C_1$–$C_6$) alkoxy;

$R_2$ represents
hydrogen or hydroxy;
$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
O($CH_2$)$_n$$CO_2$$R_8$ where n=1, 2, 3 or 4 $NR_8COR_9$, $COR_8$, $CONR_8R_9$ or $CO_2R_8$ where $R_8$ and $R_9$ are the same or different and represent hydrogen or $C_1$–$C_6$ alkyl; or
$NR_8R_9$ forms 5-, 6-, or 7-membered heterocyclic ring;

$R_3$ represents $C_1$–$C_6$ alkyl;

$R_4$ represents $C_1$–$C_6$ alkoxy; or $R_5$ and $R_6$ are the same or different and represent hydrogen or halogen;
$C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion; and X represents a bond or $CH_2O$.

Preferred compounds of Formula V are those where one of $R_5$ and $R_6$ is hydrogen. Other preferred compounds of Formula V are those where $R_4$ is methoxy, one of $R_5$ and $R_6$ is hydrogen, and the other of $R_5$ and $R_6$ is alkoxy. More preferred compounds of Formula V include those where $R_7$ is $C_4$–$C_6$ alkyl.

Particularly preferred compounds of Formula V include those where X is a bond. Other particularly preferred compounds of Formula V are those where $R_1$ is benzyl monosubstituted in the ortho position.

Other preferred compounds of the invention are represented by Formula VI

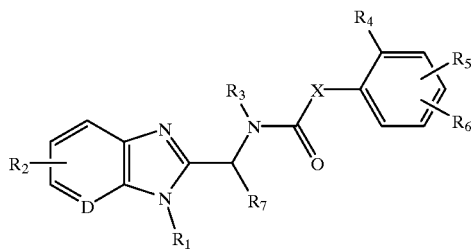

where
D is CH or N
$R_7$ is $C_1$–$C_6$ alkyl;
$R_1$ represents benzyl optionally mono-, di-, or trisubstituted independently with halogen, nitro, trifluormethyl, cyano, hydroxyl, $C_1$–$C_6$ alkoxy, or $C_1$–$C_6$ alkyl; or
amino, mono or di($C_1$–$C_6$)alkylamino, amino($C_1$–$C_6$) alkyl, or mono- or di($C_1$–$C_6$)alkylamino($C_1$–$C_6$) alkyl, or mono or di($C_1$–$C_6$)alkylamino($C_1$–$C_6$) alkoxy;

$R_2$ represents
hydrogen or hydroxy;
$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloakoxy; or
O($CH_2$)$_n$$CO_2$$R_8$ where n=1,2,3,4, $NR_8COR_9$, $COR_8$, $CONR_8R_9$, or $CO_2$ $R_8$ where $R_8$ and $R_9$ are the same or different and represent hydrogen or $C_1$–$C_6$ alkyl; or
$NR_8R_9$ forms 5-, 6-, or 7-membered heterocyclic ring;

$R_3$ represents $C_1$–$C_6$ alkyl;

$R_4$ represents $C_1$–$C_6$ alkoxy;

$R_5$ and $R_6$ are the same or different and represent hydrogen or halogen;
$C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion; and X represents a bond or $CH_2O$.

Compounds of Formula VI include compounds in which $R_4$ is methoxy, one of $R_5$ and $R_6$ is hydrogen, and the other of $R_5$ and $R_6$ is alkoxy. Other compounds of Formula VI include compounds in which $R_7$ is $C_4$–$C_6$ alkyl and compounds in which $R_7$ is $C_4$–$C_6$ alkyl and X is a bond. Also included as compounds of Formula VI are compounds in which $R_1$ is benzyl monosubstituted in the ortho position. Other compounds of Formula VI are compounds in which $R_1$ is benzyl monosubstituted in the ortho position, $R_7$ is $C_4$–$C_6$ alkyl and X is a bond.

In certain situations, the compounds of Formula I may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column.

Representative compounds of the present invention, which are encompassed by Formula I, include, but are not limited to the compounds described in the Examples and their pharmaceutically acceptable acid addition salts. In addition, if the compound of the invention is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—(CH$_2$)n-COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By "alkyl" or "lower alkyl" in the present invention is meant $C_1$–$C_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl or cyclopropylmethyl.

By "alkoxy" or "lower alkoxy" in the present invention is meant $C_1$–$C_6$ alkoxy, i.e., straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By (hetero) cyclic ring is meant a ring that is either aliphatic or aromatic and optionally contains at least one hetero atom. Hetero atoms include nitrogen, sulfur, and oxygen. Examples of such (hetero) cyclic rings are cyclohexyl, cyclopentyl, piperidinyl, piperazinyl, pyrrolidinyl, morpholinyl, etc.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, imidazolyl, (iso)quinolinyl, naphthyridinyl, benzimidazolyl, and benzoxazolyl.

As used herein, each alkyl group in a di($C_1$–$C_6$) alkylamino group is independent of the other.

Specific examples of heteroaryl groups are the following:

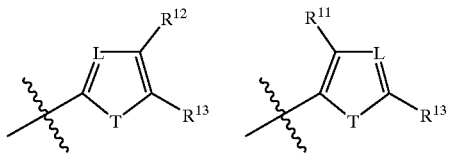

-continued

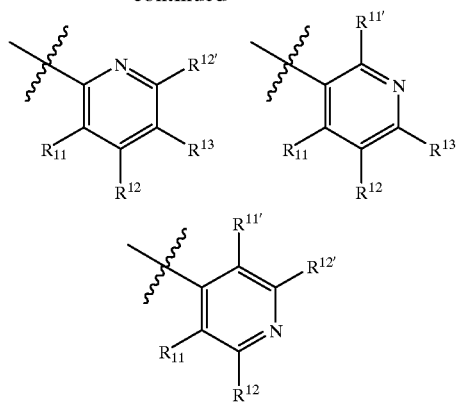

wherein
L is nitrogen or —$CR^{11}$;
T is —$NR^{19}$, oxygen, or sulfur;
$R^{11}$ and $R^{11i}$ are the same or different and are selected from hydrogen, halogen, hydroxy, $C_1$–$C_6$ alkyl, ($C_1$–$C_6$)alkoxy, amino, or mono- or di($C_1$–$C_6$) alkylamino;
$R^{12}$, $R^{12i}$, and $R^{13}$ are the same or different and are selected from hydrogen, halogen, ($C_1$–$C_6$)alkyl, ($C_1$–$C_6$)alkoxy, amino, mono- or di($C_1$–$C_6$) alkylamino, hydroxy, or trifluoromethyl; and
$R^{19}$ is hydrogen, lower alkyl having 1–6 carbon atoms.

The invention includes all possible tautomers and rotamers of the compounds represented by Formula I.

By the term "halogen" in the present invention is meant fluorine, bromine, chlorine, and iodine.

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of obesity or diabetes, a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

The present invention also pertains to packaged pharmaceutical compositions for treating disorders responsive to GLP receptor modulation, e.g., treatment obesity or diabetes. The packaged pharmaceutical compositions include a container holding a therapeutically effective amount of at least one compound of Formula I supra and instructions for using the treating disorder responsive to GLP receptor modulation in the patient.

The disclosures of all articles and references mentioned in this application, including patents, are incorporated herein by reference.

Compounds of the invention can be prepared using the reactions depicted in Schemes I to VII. The numbers appearing below or adjacent the chemical structures in these schemes refer to intermediates and are not to be confused with the compound numbers found in the examples.

Scheme 1

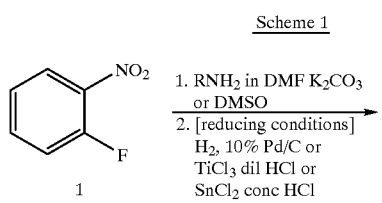

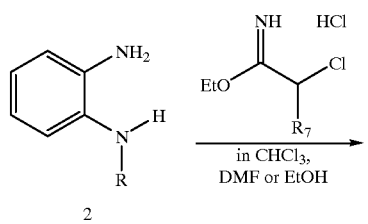

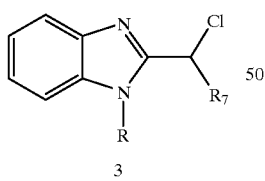

Scheme II

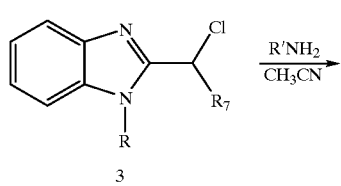

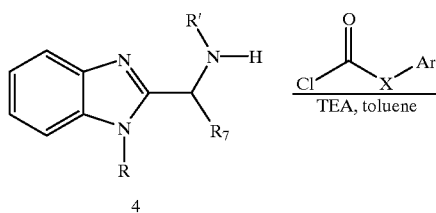

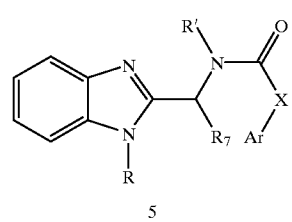

Scheme III

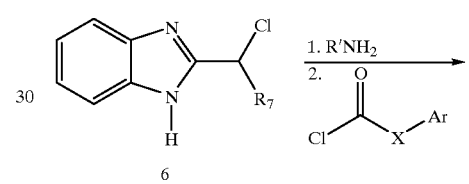

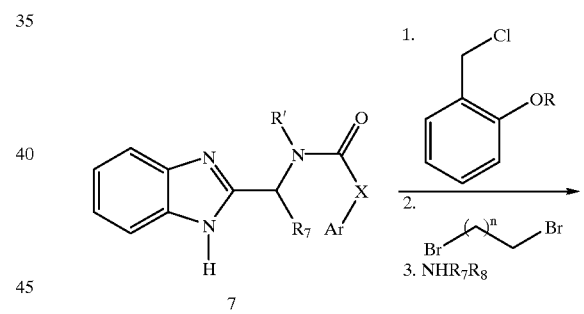

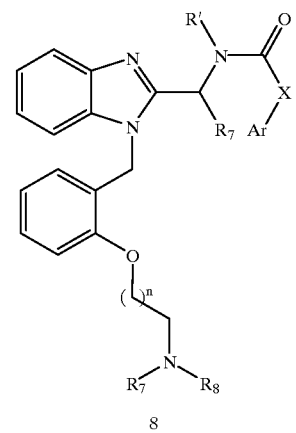

Scheme IV
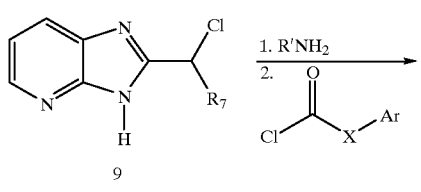
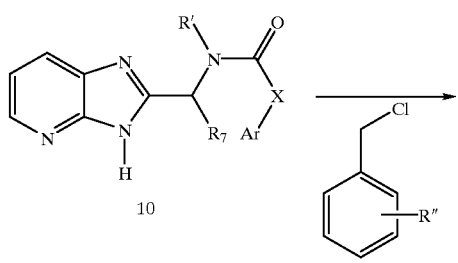
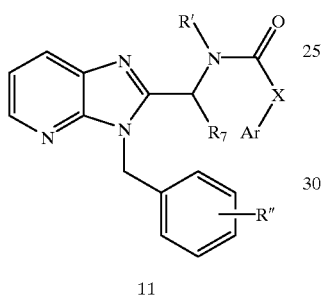
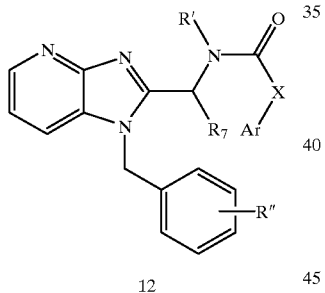
Scheme V
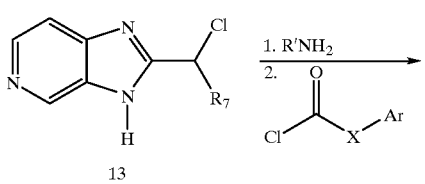
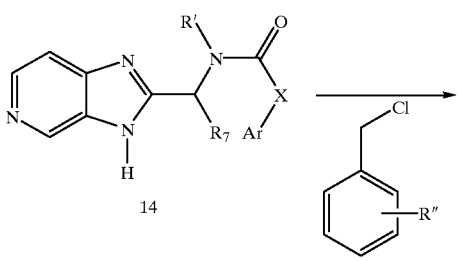
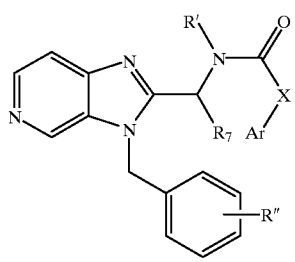
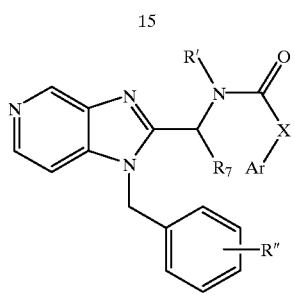
Scheme VI
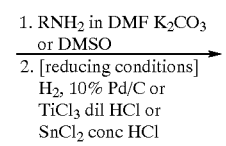
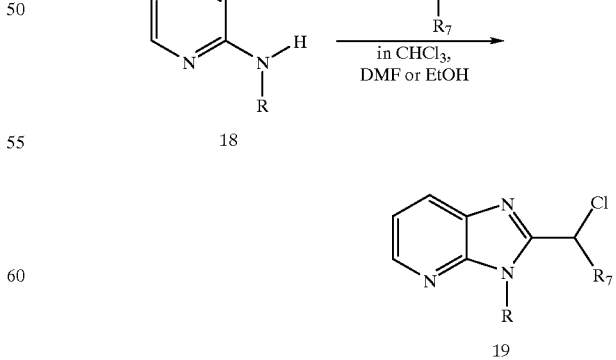

Scheme VII

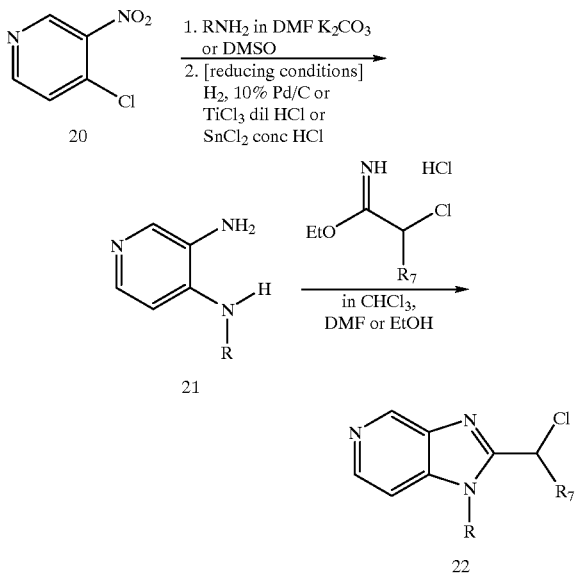

Those having skill in the art will recognize that the starting materials may be varied and additional steps employed to produce compounds encompassed by the present invention, as demonstrated by the following examples.

The following examples illustrate the general procedures for the preparation of compounds of the invention using the reactions outlined above in Schemes I–VII. These examples are not to be construed as limiting the invention in scope or spirit to the specific procedures and compounds described in them.

EXAMPLE 1

General Procedure for the Preparation of Chloromethylbenzimidazoles as Outlined in Scheme I

1. Imidate hydrochloride

A solution of 150 mL ( 2.37 mole) of chloroacetonitrile, 139 mL ( 2.37 mole) of ethanol in 1,200 mL of dry benzene is cooled to 0° C. in an ice/ethanol bath. Dry HCl gas is bubbled through the vigorously stirred solution for approximately 30 min. while the internal temperature is maintained below 10° C. The solution is allowed to stand at rt. overnight. The resulting solid is filtered and washed with 2 L of dry ether and allowed to air dry to afford 328 g (88%) of imidate hydrochloride.

2. 2-(chloromethyl)-1-[(2-methylphenyl)methyl] benzimidazole

A solution of 27 g (0.13 mole) of (2-aminophenyl) (2-methylphenyl)amine in 200 mL of anhydrous $CHCl_3$ is treated with 30.81 g (0.19 mole) of imidate at room temperature. The heterogeneous reaction mixture is allowed to stir for 1 hr. at room temperature at which time no starting material is detectable by TLC. 100 mL of saturated $NaHCO_3$ is added and extracted 3×100 mL of $CH_2Cl_2$. The extracts are dried over anhydrous $Na_2SO_4$, the solvent removed in vacuo, and the residue chromatgraphed ($SiO_2$) with 50% ethyl acetate/hexane to afford 22 g (62%) of 2-(chloromethyl)-1-[(2-methylphenyl)methyl] benzimidazole. Mass Spec $M^+$ 271.

3. 2-(chloroethyl)-1-propylbenzimidazole

A solution of 8 g (0.053 mole) of (2-aminophenyl) propylamine in 50 mL of anhydrous DMF is treated with 9.0 g (0.056 mole) of 2-chloro-1-ethoxypropanimine hydrochloride at 80° C. for 16 hr. The reaction mixture is cooled to room temperature diluted with 200 mL of ethyl acetate and washed 3×100 mL water, 1×100 mL brine, organic extracts are dried over anhydrous $Na_2SO_4$, the solvent removed in vacuo, and the residue chromatgraphed ($SiO_2$) with 30% ethyl acetate/hexane to afford 3 g (28%) of 2-(chloroethyl)-1-propylbenzimidazole.

EXAMPLE 2

General Procedure for the Preparation of Benzimidazoles as Shown in Scheme II ((2,4-dimethoxyphenyl)-N-(3-methylbutyl)-N-({1-[(2-methylphenyl)methyl]benzimidazol-2-yl}methyl)carboxamide Compound 1

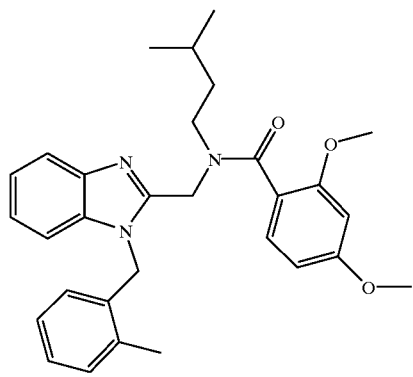

A solution of 5.4 mmole 2-(chloromethyl)-1-[(2-methylphenyl)methyl]benzimidazole in 20 mL of dry Acetonitrile is treated with 10 mL of isoamylamine for 16 hr at room temperature. The solvent is removed in vacuo and the residue is partitioned between 30 mL of ethyl acetate and 10 mL of 1 N NaOH. The ethyl acetate layer is dried over anhydrous $Na_2SO_4$ and solvent removed in vacuo to afford 1.6 g 92% ({1-[(2-methylphenyl)methyl]benzimidazol-2-yl}methyl) (3-methylbutyl)amine. 2,4-dimethoxybenzoylchloride 1.5 eq is treated with 1.0 eq of ({1-[(2-methylphenyl)methyl]benzimidazol-2-yl}methyl)(3-methylbutyl)amine in dichloromethane at room temperature for 1 hr. The reaction is quenched with 1 N NaOH and partitioned between dichloromethane and water. The organic layer is dried with $Na_2SO_4$ and the solvent removed in vacuo. The residue is chromatographed ($SiO_2$) with ethyl acetate to afford 95% of (2,4-dimethoxyphenyl)-N-({1-[(2-methylphenyl)methyl]benzimidazol-2-yl}methyl)-N-(3-methylbutyl)carboxamide (Compound 1). Mass Spec $M^+$ 486.

Following the above procedures, compounds 11, 12 and 15, 16 are prepared starting from 2-(chloromethyl)imidazolo[5,4-b]pyridine and 2-(chloromethyl)imidazolo[5,4-c]pyridine respectivly. (Cleve, G: Gibian, H.; Hoyer, G.; Rahtz, D.; Schroeder, E.; Schulz, G. *Justus Liebigs Ann. Chem.* 1971, 747, 158–171)

EXAMPLE 3

The following compounds are prepared essentially according to the procedure described in Examples 1–2, and as shown in Schemes I–VII:

(a) 2-(2,3-dimethylphenoxy)-N-methyl-N-[(1-propylbenzimidazol-2-yl)ethyl]acetamide $M^+$ 381 amu. (Compound 2)

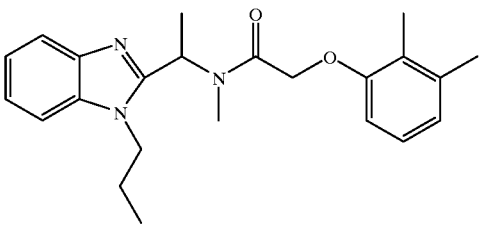

(b) 2-(2,3-dimethylphenoxy)-N-{[1-(cyclopropylmethyl)benzimidazol-2-yl]ethyl}-N-methylacetamide $M^+$ 393 amu. (Compound 3)

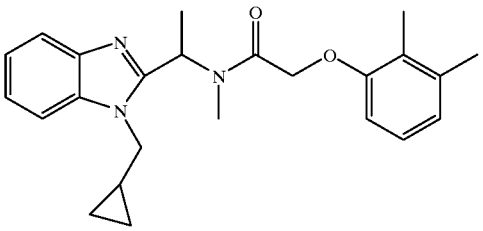

(c) (2,4-dimethoxyphenyl)-N-({1-[(2-chlorophenyl)methyl]benzimidazol-2-yl}methyl)-N-(3-methylbutyl)carboxamide $M^+$ 507 amu. (Compound 4)

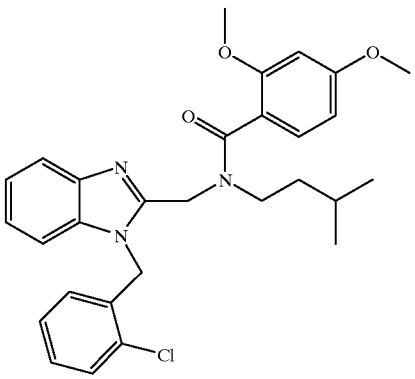

(d) (2,4-dimethoxyphenyl)-N-(3-methylbutyl)-N-({3-[(2-methylphenyl)methyl]imidazolo[4,5-b]pyridin-2-yl}methyl)carboxamide $M^+$ 488 amu. (Compound 5)

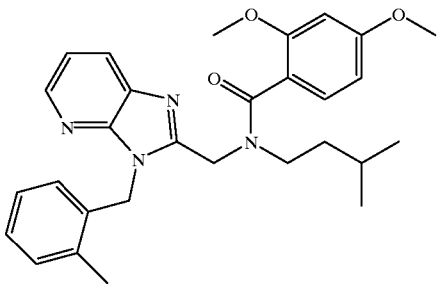

(e) 2-(2,3-dimethylphenoxy)-N-methyl-N-[(3-propylimidazolo[4,5-b]pyridin-2-yl)ethyl]acetamide $M^+$ 381 amu. (Compound 6)

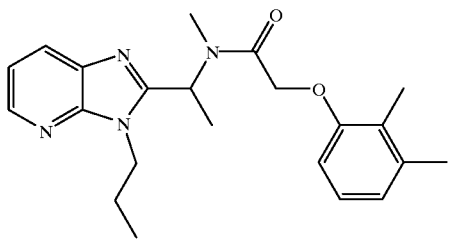

(f) 2-(2,3-dimethylphenoxy)-N-{[1-(cyclopentyl)-6-chlorobenzimidazol-2-yl]ethyl}-N-methylacetamide M+ 441 amu. (Compound 7)

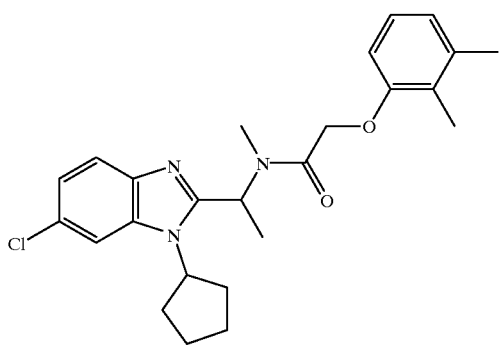

EXAMPLE 4
Assay for Glucagon-like Peptide Receptor Activation

The following assay may be used to quantitate the effects of compounds on GLP-1 activity.

Glucagon-like peptide 1 receptor activation is carried out by measuring the second messenger cyclic adenosine monophosphate (cAMP). The host cell for such studies can be any that endogenously expresses the Glp-1 receptor, such as the Rin M5F or HIT—TI5 insulinomas, or a cell line that expresses the recombinant form of that receptor. For this purpose, the appropriate cells are plated in the either 24 or 96 well plates and the cells are grown to a 75 to 95% level of confluence. Cells are usually plated 24 to 48 hours prior to assay. Immediately prior to the receptor activation study, the cells are rinsed with a phosphate buffered saline solution, and cells are incubated with from 1 to 10 mM isobutylmethylxanthine, (IBMX). The purpose of IBMX is to inhibit the enzyme cAMP phosphodiesterase, which breaks down cAMP. The use of IBMX allows one to more easily detect the ability of a hormone or drug to activate the Glp-1 receptor. In a typical assay, either the Glp-1 peptide or drug is added directly to the 24 or 96 well plate, and is incubated with the cells for up to 60 minutes at 37° C. After the desired time, the receptor activation event is terminated by the addition of hydrochloric acid to the cells, which also lyses the cells and liberates the cAMP that has accumulated within the cells. This cellular extract is harvested and neutralized with sodium hydroxide, and the cells lysates are cleared by microcentrifugation. The cell extract is then analyzed in a cAMP radioimmunoassay, such as that commercially available from NEN Life Science Products or Amersham. The amount of cAMP generated per well of cells treated with hormone or drug can be compared to that observed without the addition of such agent, to obtain an index of receptor activation. Dose-response curves are also performed to obtain the level of potency and efficacy of any test compound.

In the described assay, preferred compounds of the invention will have 5% or greater stimulation with respect to GLP-1.

EXAMPLE 5

Glucose Tolerance Test

Following overnight fasting adult male (200–300 g) Sprague-Dawley rats are injected orally with either vehicle or glucose solution in a given concentration. Following thirty-five minutes of resting in their home cages, the animals are brought back into the laboratory and restrained using a BRAINTREE SCIENTIFIC adjustable restrainer. Within five minutes of restraint, one of the lateral tail veins is catheterized, and the animals are given intravenous (iv) injection of either glucagon-like polypeptide 1 (GLP1) or test compound. Five minutes after iv injection, the animals are euthanized by decapitation, and trunk blood is collected in tubes containing EDTA. The plasma levels of insulin and glucose measured using appropriate radio-immunoassay (RIA) kits.

EXAMPLE 6

Streptozocin-Induced Diabetes Glucose Tolerance Test

Streptozotocin is an antibiotic extracted from *Streptomyces achromogenes*, which when injected into animals, causes pancreatic β-cell degranulation and necrosis. To achieve mild necrosis of pancreatic β-cells, which induces a state of diabetes without affecting normal development and weight gain, a 35 mg/kg/5 ml dose STZ is injected intraperitoneally (ip) into a group of healthy, naive animals. The control group animals receive 0.1 N citrate buffer (vehicle, 5 ml/kg, 10=16). Five days after ip injections (day5), the diabetic symptoms are assessed via the following test of glucose tolerance. All animals receive an oral injection of 3 g/kg/10 ml glucose solution between 3:00 and 5:00 PM. Forty minutes later, their blood glucose levels are measured using the LIFE SCAN ONE TOUCH glucose monitoring system. Animals are restrained and a blood sample is taken from a lateral tail vein. Animals that show substantially higher blood glucose levels (100 to 250% higher than non-STZ treated animals, normally ⅔ of STZ treated animals) are used to assess the effects of test compounds in this animal model of diabetes. On day 7, following overnight fast, the animals are subjected to glucose tolerance test using a procedure identical to that described above. The test compound is injected iv or orally and IV injection of GLP-1 is used as a positive control.

EXAMPLE 7

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

EXAMPLE 8

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed:

1. A compound of the formula:

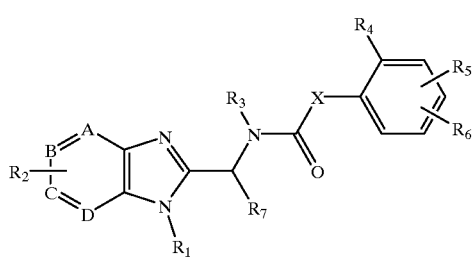

I or pharmaceutically acceptable non-toxic salts thereof wherein:
$R_7$ represents H, or $C_1$–$C_6$ alkyl;
when $R_7$ is H, $R_1$ is not 3-fluorobenzyl and $R_1$ represents
2-, 3-, or 4-picolyl or benzyl, each of which is optionally mono-, di-, or trisubstituted independently with
halogen, nitro, trifluoromethyl, cyano, hydroxyl, $C_1$–$C_6$ alkoxy, or $C_1$–$C_6$ alkyl;
amino, mono or di($C_1$–$C_6$)alkylamino, amino($C_1$–$C_6$) alkyl, or mono- or di($C_1$–$C_6$)alkylamino($C_1$–$C_6$) alkyl, or mono- or di ($C_1$–$C_6$)alkylamino($C_1$–$C_6$) alkoxy;
—O($CH_2$)$_n$$CO_2R_8$ where n is 1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl or $NR_8R_9$ forms a 5-, 6- or 7-membered heterocycloalkyl ring;

$SO_2R_8$, $NHSO_2R_8$, $SO_2NHR_8$, $SO_2NHCOR_8$, $CONHSO_2R_8$ where $R_8$ is as defined above;
O($CH_2$)$_n$-G where n=1,2,3,4 and G represents $SO_2R_8$, $NHSO_2R_8$, $SO_2NHR_8$, $SO_2NHCOR_8$, $CONHSO_2R_8$, where $R_8$ is as defined above; or
tetrazole, triazole, imidazole, thiazole, oxazole, thiophene, or pyridyl; and
when $R_7$ represents $C_1$–$C_6$ alkyl, $R_1$ represents $C_1$–$C_6$ alkyl, cyclopentyl, or cyclopropylmethyl; and
$R_2$ represents
hydrogen or hydroxy;
$C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
O($CH_2$)$_n$$CO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl or $NR_8R_9$ forms 5-, 6-, or 7-membered heterocyclic ring;
$R_3$ represents $C_1$–$C_6$ alkyl;
$R_4$ represents $C_1$–$C_6$ alkoxy; or
$R_4$ can represent methyl when $R_1$ and $R_7$ are lower alkyl;
$R_5$ and $R_6$ are the same or different and represent
hydrogen or halogen;
$C_1$–$C_6$ alkyl or $C_1$–$C_6$ alkoxy, the alkyl portion of each being optionally substituted with amino, mono- or di($C_1$–$C_6$)alkylamino, or a $C_5$–$C_7$ heterocycloalkyl group where the heteroatom is nitrogen and the nitrogen is attached to the parent alkyl portion;
O($CH_2$)$_n$$CO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms or $NR_8R_9$ forms a 5-, 6- or 7-membered heterocyclic ring; toms or $NR_8R_9$ forms a 5-, 6- or 7-membered heterocyclic ring;
X represents a bond, $CH_2O$, or $CH=CH$; and
A, B, C, and D are the same or different and represent CH or N with the proviso that not more than two of A, B, C and D represent N.

2. A compound of the formula

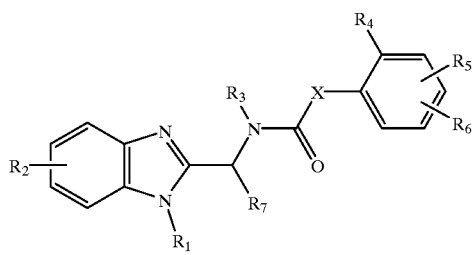

where
$R_7$ is $C_1$–$C_6$ alkyl;
$R_1$ represents benzyl optionally mono-, di-, or trisubstituted independently with
halogen, nitro, trifluoromethyl, cyano, hydroxyl, $C_1$–$C_6$ alkoxy, or $C_1$–$C_6$ alkyl; or
amino, mono or di($C_1$–$C_6$)alkylamino, amino($C_1$–$C_6$) alkyl, or mono- or di($C_1$–$C_6$)alkylamino($C_1$–$C_6$) alkyl, or mono- or di ($C_1$–$C_6$)alkylamino($C_1$–$C_6$) alkoxy;

$R_2$ represents
   hydrogen or hydroxy;
   $C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
   $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl or $NR_8R_9$ forms 5-, 6-, or 7-membered heterocyclic ring;

$R_3$ represents $C_1$–$C_6$ alkyl;
$R_4$ represents $C_1$–$C_6$ alkoxy;
$R_5$ and $R_6$ are the same or different and represent
   hydrogen or halogen;
   $C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion; and
X represents a bond or $CH_2O$.

3. A compound according to claim 2, wherein one of $R_5$ and $R_6$ is hydrogen.

4. A compound according to claim 2, wherein $R_4$ is methoxy, one of $R_5$ and $R_6$ is hydrogen, and the other of $R_5$ and $R_6$ is alkoxy.

5. A compound according to claim 2, wherein $R_7$ is $C_4$–$C_6$ alkyl.

6. A compound according to claim 5, wherein X is a bond.

7. A compound according to claim 2, wherein $R_1$ is benzyl monosubstituted in the ortho position.

8. A compound according to claim 7, wherein $R_7$ is $C_4$–$C_6$ alkyl and X is a bond.

9. A compound of the formula:

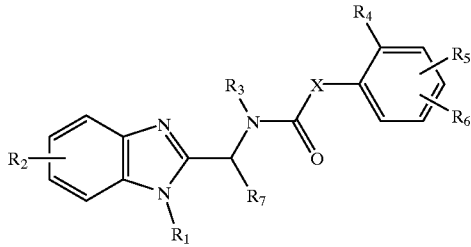

wherein:
$R_7$ represents $C_1$–$C_6$ alkyl;
$R_1$ represents $C_1$–$C_6$ alkyl, cyclopentyl, or cyclopropylmethyl;
$R_2$ represents
   hydrogen or hydroxy;
   $C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
   $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl or $NR_8R_9$ forms 5-, 6-, or 7-membered heterocyclic ring;

$R_3$ represents $C_1$–$C_6$ alkyl;
$R_4$ represents $C_1$–$C_6$ alkoxy; or
$R_4$ can represent methyl when $R_1$ and $R_7$ are lower alkyl;
$R_5$ and $R_6$ are the same or different and represent
   hydrogen or halogen;
   $C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion;
   $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or straight or branched chain lower alkyl having 1–6 carbon atoms or $NR_8R_9$ forms a 5-, 6- or 7-membered heterocyclic ring;

X represents a bond or $CH_2O$.

10. A compound according to claim 9 wherein $R_3$ and $R_7$ are methyl.

11. A compound according to claim 9 wherein $R_1$ is propyl or cyclopropylmethyl.

12. A compound according to claim 9 wherein $R_1$ is cyclopentyl.

13. A compound according to claim 9 wherein X is $CH_2O$.

14. A compound according to claim 13, wherein $R_1$ is propyl or cyclopropylmethyl.

15. A compound according to claim 9, wherein $R_1$ is propyl or cyclopropylmethyl and one of $R_5$ and $R_6$ is hydrogen.

16. A compound according to claim 9, wherein $R_1$ is propyl, $R_4$ is methoxy or methyl, one of $R_5$ and $R_6$ is hydrogen, and the other of $R_5$ and $R_6$ is alkoxy.

17. A compound of the formula:

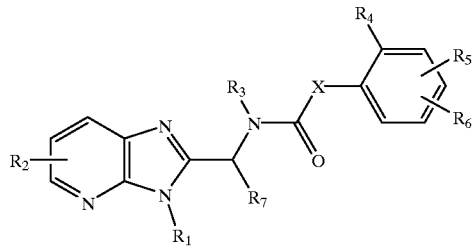

wherein:
$R_7$ represents $C_1$–$C_6$ alkyl;
$R_1$ represents $C_1$–$C_6$ alkyl, cyclopentyl, or cyclopropylmethyl;
$R_2$ represents
   hydrogen or hydroxy;
   $C_1$–$C_6$ alkyl or $C_1$–$C_6$ alkoxy, each of which is optionally substituted with amino or mono- or di($C_1$–$C_6$) alkylamino, $C_5$–$C_7$ cycloalkylamino or $C_5$–$C_7$ cycloalkoxy; or
   $O(CH_2)_nCO_2R_8$ where n=1,2,3,4, $NR_8COR_9$, $COR_8$, $CONR_8R_9$ or $CO_2R_8$ where $R_8$ and $R_9$ are the same or different and represent hydrogen or $C_1$–$C_6$ alkyl or $NR_8R_9$ forms 5-, 6-, or 7-membered heterocyclic ring;

$R_3$ represents $C_1$–$C_6$ alkyl;
$R_4$ represents $C_1$–$C_6$ alkoxy; or
$R_4$ can represent methyl when $R_1$ and $R_7$ are lower alkyl;
$R_5$ and $R_6$ are the same or different and represent
   hydrogen or halogen;
   $C_1$–$C_6$ alkyl or $C_1$–$C_6$ alkoxy, the alkyl portion of each being optionally substituted with amino, mono- or di($C_1$–$C_6$) alkylamino, or a $C_5$–$C_7$ heterocycloalkyl group where the heteroatom is nitrogen and the nitrogen is attached to the parent alkyl portion;

O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or straight or branched chain lower alkyl having 1–6 carbon atoms or NR$_8$R$_9$ forms a 5-, 6- or 7-membered heterocyclic ring;

X represents a bond or CH$_2$O.

18. A compound according to claim 17 wherein R$_3$ and R$_7$ are methyl.

19. A compound according to claim 17 wherein R$_1$ is propyl or cyclopropylmethyl.

20. A compound according to claim 17 wherein R$_1$ is cyclopentyl.

21. A compound according to claim 17 wherein X is CH$_2$O.

22. A compound according to claim 21, wherein R$_1$ is propyl or cyclopropylmethyl.

23. A compound according to claim 17, wherein R$_1$ is propyl or cyclopropylmethyl and one of R$_5$ and R$_6$ is hydrogen.

24. A compound according to claim 17, wherein R$_1$ is propyl, R$_4$ is methoxy or methyl, one of R$_5$ and R$_6$ is hydrogen, and the other of R$_5$ and R$_6$ is alkoxy.

25. A compound of the formula

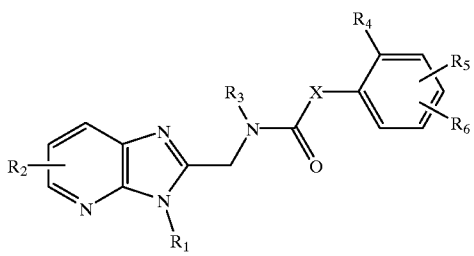

where
R$_1$ represents benzyl optionally mono-, di-, or trisubstituted independently with
halogen, nitro, trifluoromethyl, cyano, hydroxyl, C$_1$–C$_6$ alkoxy, or C$_1$–C$_6$ alkyl; or
amino, mono or di(C$_1$–C$_6$)alkylamino, amino(C$_1$–C$_6$) alkyl, or mono- or di(C$_1$–C$_6$)alkylamino(C$_1$–C$_6$) alkyl, or mono- or di(C$_1$–C$_6$)alkylamino(C$_1$–C$_6$) alkoxy;

R$_2$ represents
hydrogen or hydroxy;
C$_1$–C$_6$ alkyl or C$_1$–C$_6$ alkoxy, each of which is optionally substituted with amino or mono- or di(C$_1$–C$_6$) alkylamino, C$_5$–C$_7$ cycloalkylamino or C$_5$–C$_7$ cycloalkoxy; or
O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or C$_1$–C$_6$ alkyl or NR$_8$R$_9$ forms 5-, 6-, or 7-membered heterocyclic ring;

R$_3$ represents C$_1$–C$_6$ alkyl;
R$_4$ represents C$_1$–C$_6$ alkoxy;
R$_5$ and R$_6$ are the same or different and represent
hydrogen or halogen;
C$_1$–C$_6$ alkyl or C$_1$–C$_6$ alkoxy, the alkyl portion of each being optionally substituted with amino, mono- or di(C$_1$–C$_6$) alkylamino, or a C$_5$–C$_7$ heterocycloalkyl group where the heteroatom is nitrogen and the nitrogen is attached to the parent alkyl portion; and X represents a bond or CH$_2$O.

26. A compound according to claim 25, wherein one of R$_5$ and R$_6$ is hydrogen.

27. A compound according to claim 25, wherein R$_4$ is methoxy, one of R$_5$ and R$_6$ is hydrogen, and the other of R$_5$ and R$_6$ is alkoxy.

28. A compound according to claim 25, wherein X is a bond.

29. A compound according to claim 25, wherein R$_1$ is benzyl monosubstituted in the ortho position.

30. A compound according to claim 1, which is ((2,4-dimethoxyphenyl)-N-(3-methylbutyl)-N-({1-[(2-methylphenyl)methyl]benzimidazol-2-yl}methyl) carboxamide.

31. A compound according to claim 1, which is 2-(2,3-dimethylphenoxy)-N-methyl-N-[(1-propylbenzimidazol-2-yl)ethyl]acetamide.

32. A compound according to claim 1, which is 2-(2,3-dimethylphenoxy)-N-{[1-(cyclopropylmethyl) benzimidazol-2-yl]ethyl}-N-methylacetamide.

33. A compound according to claim 1, which is (2,4-dimethoxyphenyl)-N-({1-[(2-chlorophenyl)methyl] benzimidazol-2-yl}methyl)-N-(3-methylbutyl) carboxamide.

34. A compound according to claim 1, which is (2,4-dimethoxyphenyl)-N-(3-methylbutyl)-N-({3-[(2-methylphenyl)methyl]imidazolo[4,5-b]pyridin-2-yl}methyl)carboxamide.

35. A compound according to claim 1, which is 2-(2,3-dimethylphenoxy)-N-methyl-N-[(3-propylimidazolo[4,5-b] pyridin-2-yl)ethyl]acetamide.

36. A compound according to claim 1, which is 2-(2,3-dimethylphenoxy)-N-{[1-(cyclopentyl)-6-chlorobenzimidazol-2-yl]ethyl}-N-methylacetamide.

37. A pharmaceutical composition comprising a compound as claimed in claim 1 and a pharmaceutically acceptable carrier or excipient.

38. A method of treating diabetes, comprising administering to a patient in need of such treatment an effective amount of a compound according to claim 1, or a pharmaceutically acceptable salt thereof.

39. A method of treating obesity or eating disorders, comprising administering to a patient in need of such treatment an effective amount of a compound according to claim 1, or a pharmaceutically acceptable salt thereof.

40. A packaged pharmaceutical composition comprising the pharmaceutical composition of claim 37 in a container and instructions for using the composition to treat a patient suffering from a disorder responsive to modulation of blood glucose levels.

41. The packaged pharmaceutical composition of claim 40, wherein said patient is suffering from obesity or diabetes.

42. A compound of the formula:

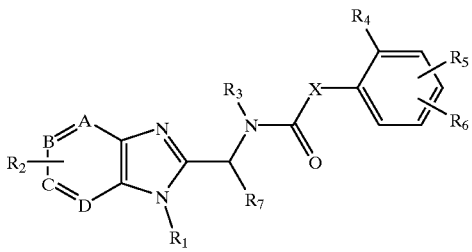

or pharmaceutically acceptable non-toxic salts thereof wherein:
R$_7$ represents H, or C$_1$–C$_6$ alkyl;
when R$_7$ is H, R$_1$ is not 3-fluorobenzyl and R$_1$ represents 2-, 3-, or 4-picolyl or benzyl, each of which is optionally mono-, di-, or trisubstituted independently with halogen, nitro, trifluoromethyl, cyano, hydroxyl, $C_1-C_6$ alkoxy, or $C_1-C_6$ alkyl;

amino, mono or di($C_1-C_6$)alkylamino, amino($C_1-C_6$) alkyl, or mono- or di($C_1-C_6$)alkylamino($C_1-C_6$) alkyl, or mono- or di($C_1-C_6$)alkylamino($C_1-C_6$) alkoxy;

—O(CH$_2$)$_n$CO$_2$R$_8$ where n is 1,2,3,4, NR$_8$COR$_9$, COR$_8$, CONR$_8$R$_9$ or CO$_2$R$_8$ where R$_8$ and R$_9$ are the same or different and represent hydrogen or $C_1-C_6$ alkyl or NR$_8$R$_9$ forms a 5-, 6- or 7-membered heterocycloalkyl ring;

SO$_2$R$_8$, NHSO$_2$R$_8$, SO$_2$NHR$_8$, SO$_2$NHCOR$_8$, CONHSO$_2$R$_8$ where R$_8$ is as defined above;

O(CH$_2$)$_n$—G where n=1,2,3,4 and G represents SO$_2$R$_8$, NHSO$_2$R$_8$, SO$_2$NHR$_8$, SO$_2$NHCOR$_8$, CONHSO$_2$R$_8$, where R$_8$ is as defined above; or tetrazole, triazole, imidazole, thiazole, oxazole, thiophene, or pyridyl;

when R$_7$ represents $C_1-C_6$ alkyl, R$_1$ represents $C_1-C_6$ alkyl, cyclopentyl, or cyclopropylmethyl; or R$_1$ represents benzyl optionally mono-, di-, or trisubstituted independently with halogen, nitro, trifluoromethyl, cyano, hydroxyl, $C_1-C_6$ alkoxy, or $C_1-C_6$ alkyl; or amino, mono or di($C_1-C_6$)alkylamino, amino($C_1-C_6$)alkyl, or mono- or di($C_1-C_6$)alkylamino ($C_1-C_6$)alkyl, or mono- or di($C_1-C_6$)alkylamino ($C_1-C_6$)alkoxy;

R$_2$ represents
hydrogen or hydroxy;
$C_1-C_6$ alkyl or $C_1-C_6$ alkoxy, each of which is optionally substituted with amino or mono- or di($C_1-C_6$) alkylamino, $C_5-C7$ cycloalkylamino or $C_5-C_7$ cycloalkoxy; or O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or $C_1-C_6$ alkyl; or NR$_8$R$_9$ forms 5-, 6-, or 7-membered heterocyclic ring;

R$_3$ represents $C_1-C_6$ alkyl;
R$_4$ represents $C_1-C_6$ alkoxy; or
R$_4$ represents methyl when R$_1$ and R$_7$ are lower alkyl;
R$_5$ and R$_6$ are the same or different and represent hydrogen or halogen;
$C_1-C_6$ alkyl or $C_1-C_6$ alkoxy, the alkyl portion of each being optionally substituted with amino, mono- or di($C_1-C_6$)alkylamino, or a $C_5-C_7$ heterocycloalkyl group where the heteroatom is nitrogen and the nitrogen is attached to the parent alkyl portion;

O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or straight or branched chain lower alkyl having 1–6 carbon atoms;

NR$_8$R$_9$ forms a 5-, 6- or 7-membered heterocyclic ring;

X represents a bond, CH$_2$O, or CH=CH; and
A, B, C, and D are the same or different and represent CH or N with the proviso that not more than two of A, B, C and D represent N.

43. A method for localizing receptors in a tissue sample comprising:
contacting with the sample a detectably-labeled compound of claim 42 under conditions that permit binding of the compound to the receptors, washing the sample to remove unbound compound, and detecting the bound compound.

44. The method of claim 43, wherein the receptors modulate blood glucose levels.

45. The method of claim 43, wherein the receptors are GLP-1 receptors.

46. A pharmaceutical composition comprising a compound as claimed in claim 42 and a pharmaceutically acceptable carrier or excipient.

47. A method of treating diabetes, comprising administering to a patient in need of such treatment an effective amount of a compound according to claim 42, or a pharmaceutically acceptable salt thereof.

48. A method of treating obesity or eating disorders, comprising administering to a patient in need of such treatment an effective amount of a compound according to claim 42, or a pharmaceutically acceptable salt thereof.

49. A compound of the formula

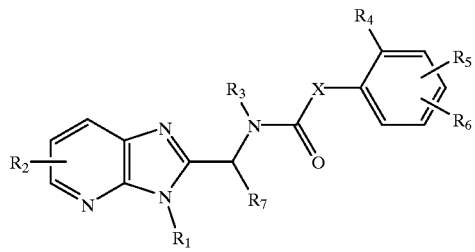

where
R$_7$ is hydrogen $C_1-C_6$ alkyl;
R$_1$ represents benzyl optionally mono-, di-, or trisubstituted independently with
halogen, nitro, trifluoromethyl, cyano, hydroxyl, $C_1-C_6$ alkoxy, or $C_1-C_6$ alkyl; or
amino, mono or di($C_1-C_6$)alkylamino, amino($C_1-C_6$) alkyl, or mono- or di($C_1-C_6$)alkylamino($C_1-C_6$) alkyl, or mono- or di($C_1-C_6$)alkylamino($C_1-C_6$) alkoxy;

R$_2$ represents
hydrogen or hydroxy;
$C_1-C_6$ alkyl or $C_1-C_6$ alkoxy, each of which is optionally substituted with amino or mono- or di($C_1-C_6$) alkylamino, $C_5-C_7$ cycloalkylamino or $C_1-C_7$ cycloalkoxy; or O(CH$_2$)$_n$CO$_2$R$_8$ where n=1,2,3,4, NR$_8$COR$_9$, COR$_8$, CONR$_8$R$_9$ or CO$_2$R$_8$ where R$_8$ and R$_9$ are the same or different and represent hydrogen or $C_1-C_6$ alkyl or NR$_8$R$_9$ forms 5-, 6-, or 7-membered heterocyclic ring;

R$_3$ represents $C_1-C_6$ alkyl;
R$_4$ represents $C_1-C_6$ alkoxy;
R$_5$ and R$_6$ are the same or different and represent hydrogen or halogen; or
$C_1-C_6$ alkyl or $C_1-C_6$ alkoxy, the alkyl portion of each being optionally substituted with amino, mono- or di($C_1-C_6$) alkylamino, or a $C_5-C_7$ heterocycloalkyl group where the heteroatom is nitrogen and the nitrogen is attached to the parent alkyl portion; and
X represents a bond or CH$_2$O.

50. A compound according to claim 49, wherein R$_7$ is $C_4-C_6$ alkyl.

51. A compound according to claim 49, wherein R$_1$ is benzyl monosubstitued in the ortho position, R$_7$ is $C_4-C_6$ alkyl and X is a bond.

* * * * *